United States Patent [19]

Kurz

[11] 4,229,165

[45] * Oct. 21, 1980

[54] PULSATING ORTHODONTIC APPLIANCE

[76] Inventor: Craven H. Kurz, 10921 Wilshire Blvd., Suite 512, Los Angeles, Calif. 90024

[*] Notice: The portion of the term of this patent subsequent to Nov. 7, 1995, has been disclaimed.

[21] Appl. No.: 895,438

[22] Filed: Apr. 11, 1978

Related U.S. Application Data

[63] Continuation-in-part of Ser. No. 717,090, Aug. 24, 1976, abandoned.

[51] Int. Cl.³ .............................................. A61C 7/00
[52] U.S. Cl. .......................................... 433/24; 433/5
[58] Field of Search ............. 32/14 D, 14 E, DIG. 4, 32/20; 128/62 A, 24 A; 433/5, 24

[56] References Cited

U.S. PATENT DOCUMENTS 3,903,604  9/1975  Snead .................................. 32/14 D
4,123,844  11/1978  Kurz .................................... 32/14 D Primary Examiner—Louis G. Mancene
Attorney, Agent, or Firm—Keith D. Beecher

[57] ABSTRACT

An orthodontic process is provided by which a pulsating force is applied to the tooth to be moved, rather than a continuous force as in the case with the prior art methods. The invention is predicted on the concept that when pulsating forces are applied to the tooth, there is little or no hyalinization and consequently more cellular activity, giving rise to more oesteoclastic activity for bone resorption and more oesteoblastic activity for bone opposition. Moreover, the pulsational effect on the tooth on the adjacent periodontal membrane and bone tends to loosen their fibrous structure, and helps the tooth to find a path of least resistance through the bone.

1 Claim, 10 Drawing Figures

PULSATING ORTHODONTIC APPLIANCE

This application is a continuation-in-part of copending application Ser. No. 717,090, now abandoned, filed Aug. 24, 1976.

BACKGROUND OF THE INVENTION

The conventional method of orthodontic tooth movement, as practiced in the prior art, has been one of constant pressure applied to the tooth in order to move the tooth through the adjacent bone. Constant pressure applied to the periodontal membrane by traditional orthodontic appliances causes the periodontal fibers to become cell-free which results in stand-still of the tooth. Compression of tissue results in reduced blood supply and tissue necrosis, and the tooth will not move again until the bone subjacent to the hyalinized tissue has been eliminated by undermining resorption. Generally, it is essentially the magnitude of the force which will determine the duration of the hyalinization. Moreover, strong forces produce a wide hyalinization area of long duration. A discussion of this phenomena may be found on pages 76 and 97 of Current Orthodontic Concepts and Techniques, T. M. Graber, Editor, published by W. B. Saunders & Co., 1969.

When a tooth is tipped by a continuous force exerted on it by a usual prior art orthodontic appliance, the periodontal membrane is compressed in a circumscribed area situated close to the alveolar crest. This area becomes cell-free and the blood vessels are occluded, and oesteoclastic activity is reduced to a minimum. A description of this occurrence may be found, for example, at page 497 of Orthodontic Principles and Practice by Graber, Second Edition, published by Saunders & Co., 1967. If the pressure area of the periodontal membrane during the movement of a tooth by an orthodontic device is not compressed by strong forces, then the formation of oesteoclasts, the cells responsible for resorption of bone, will be enhanced. The flow of blood to the area will not be restricted, and consequently oesteoclastic activity will be more vigorous and bone resorption will be increased.

As stated above, the orthodontic appliance of the present invention introduces pressure impulses to the tooth being moved, rather than a continuous force. With every pressure impulse from the appliance of the invention, the tissue pressure in the periodontal membrane and adjacent bone tissue will be increased. When the pressure is relaxed, the tissue pressure in the periodontal membrane and adjacent bone tissue will be reduced. This fluctuation from high pressure to low pressure in the periodontal and adjacent tissue will result in a pump-like action that will suck blood and tissue fluid into the area, and will then expel fluid from the area, for each cycle of operation. This serves to increase the cellular action around the moving tooth, giving rise to more oesteoclasts for bone resorption and more oesteoblasts for bone apposition.

The active exchange of fluid during the pulsating operation of the appliance of the invention helps carry the by-products of bone resorption out of the resorption area. The pulsating tooth movement produced by the appliance of the invention is physiological and dynamic in nature, rather than pathological. Because the pulsation pressure exerted by the appliance of the invention does not result in areas of hyalinization and necrosis, there is no root resorption or horizontal bone loss during the operation. The pump-like action of the tooth being pulsated by the appliance of the invention is the same on the tension side of the tooth as on the compression side, but opposite in the timing cycle. On the tension side of the tooth, the increased blood supply results in increased cellular activity. The bone building cell is the oesteoblast. The oesteoblastic activity acts in a maximal manner during pulsating tooth movement, resulting in increased bone formation and active stabilization.

To reiterate, pulsation pressure optimal in magnitude and frequency, as produced by the appliance of the invention, is the ideal force for tooth movement because blood supply to the adjacent tissue is not reduced, but due to cyclic positive and negative tissue fluid pressures, a pump-like action is set up in the tissue creating greater blood supply. This enhanced blood supply results in increased oesteoclastic cellular action for the resorption of bone and increased oesteoblastic cellular action for the deposition of new bone elements. Greater tissue exchange in the area of tooth movement to enhance the removal of bone breakdown products, and to enhance the supply of elements necessary for the formation of new bone; and little or no areas of hyalinization or necrosis of tissue, so that root resorption by cementum necrosis does not occur.

The pulsation or vibrational nature of the force applied to the tooth by the appliance of the invention also helps to break down tissue resistance, as mentioned above. The fibrous elements of the adjacent tissue tend to give way more easily to the moving tooth mass, as the tooth is vibrated, and the tooth moves along the path of least resistance. The vibrating tooth mass more easily separates the fibrous elements and moves more easily through the adjacent bone. The increased circulation and vibrational effect occurs not only in the local area, but flows to adjacent tissues to aid in their adjustment, as teeth are moved through bone, and the total boney architecture is changed.

As a result, the use of the pulsating orthodontic appliance of the present invention results in faster movement of the tooth; reduction of root resorption during orthodontic movement; reduction of horizontal bone loss during bone reconstruction; reduced discomfort from heavy orthodontic pressures; and reduction in tooth extrusion from their boney sockets when pressurized.

The total effect resulting from the use of the orthodontic appliance of the invention is that tooth movement is of a physiological nature causing little or no irreversible results to the tooth or horizontal bone level, and expediting the travel of the tooth along its path through the adjacent bone so as to obtain the most rapid orthodontic movement in a painless environment.

Most orthodontic problems of dental protrusion and/or tooth size arch length discrepancies can be corrected by the use of the pulsating appliance of the present invention. Moreover, the conventional therapy of bicuspid extraction is eliminated when the appliance of the invention is used and, instead, third molars may be extracted and all posterior teeth moved distally.

BRIEF DESCRIPTION OF THE DRAWINGS

FIG. 3 shows an implementation of the process of the invention as applied to an extra oral face mask appliance;

FIG. 4 is a representation of an implementation of the process of the invention embodying a maxillary palatal intraoral appliance;

FIG. 5 is an implementation of the process of the invention applied to a mandibular intraoral appliance;

FIG. 6 is a representation of an hydraulic fluid implementation of the process of the invention;

FIG. 7 is a section taken essentially along the line 7—7 of FIG. 6;

FIG. 8 is a representation, partly in section, of a second hydraulic fluid appliance implementing the process of the invention;

FIG. 9 is a representation of the appliance of FIG. 8 incorporated into a maxillary palatal orthodontic device; and FIG. 10 is a representation of the appliance of FIG. 8 incorporated into a mandibular orthodontic device.

DETAILED DESCRIPTION OF THE ILLUSTRATED EMBODIMENTS

Figure 1:
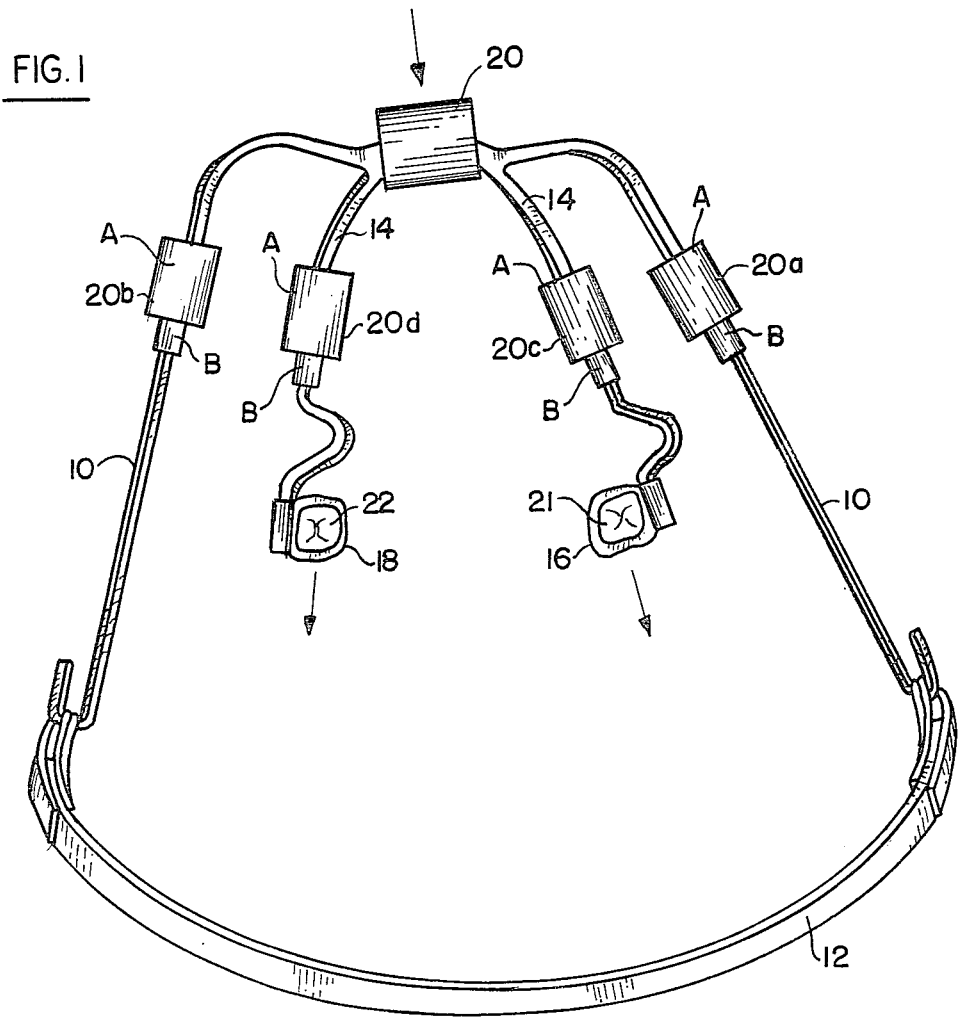
FIG. 1 shows one implementation of the process of the invention as applied to a posterior cervical extra oral appliance.
Figure 2:
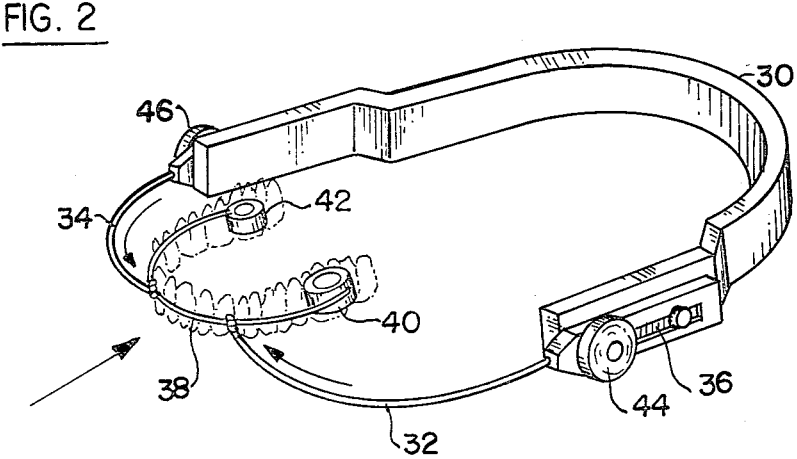
FIG. 2 shows an implementation of the process of the invention as applied to an anterior cervical extra oral appliance.

In the embodiments illustrated in FIGS. 1, 2 and 3, the process of the present invention is incorporated into various types of cervical extra oral appliances. In these embodiments, a vibrating or pulsating unit is attached to, or is part of, the regular cervical extra oral headgear appliance. The pulsating unit delivers pulsations to the upper or lower posterior teeth through attachments which connect the teeth to the extra oral appliance. In these embodiments, the pulsating unit is prefeably electrical, and it is energized by its own battery-operated motor to activate the extra oral appliance while it is being worn. The motor battery is preferably rechargeable, so that it may be recharged from a conventional 120-volt receptacle, through an appropriate recharging unit, when the appliance is not being worn. Miniature battery-operated pulsating electric motors are available on the market which are suitable for the purpose. The resulting pulsating cervical extra oral appliances, incorporating the concepts of the invention, may be used to direct a pulsation pressure to the molars in a distal direction. The pulsation pressure may be used to move the maxillary or mandibular molars individually, or both simultaneously.

Once the posterior teeth have been moved distally by the appliance, then the anterior teeth may be moved distally by elastic or spring pressure that uses the distally moved molars as anchorage, such as shown in the embodiments of FIGS. 4 and 5. It may be necessary to extract the third molars to make room for the first and second molars as they move distally.

The present invention makes it possible to correct maxillary or mandibulator dental protrusion and/or tooth size arch length discrepancies without bicuspid extraction. Instead of removing teeth in the arch, such as the bicuspids, which has been customary in the prior art orthodontic treatment, only third molar extractions are required when the appliance of the present invention is used, followed by the pulsational movement of the first and second molars distally to correct orthodontic dental protrusions and/or arch length deficiency problems.

The appliance shown in FIG. 1 is a posterior cervical extra oral appliance which includes the usual external extra oral arch bow 10 which is hooked to a usual elastic retaining band 12. The band 12 extends around the head or neck of the wearer. The appliance of FIG. 1 also includes an intra oral internal arch bow 14. The ends of bow 14 are coupled to usual tooth bands 16 and 18 which are mounted on molars 21 and 22 which are to be moved distally.

In accordance with the present invention, a battery-operated electric pulsating motor 20 is mounted, for example, at the junction of the external and internal bows, so that a pulsating pressure may be exerted on the molars 21 and 22 through the arch bow 14. As an alternative, a pair of pulsating motors 20a and 20b may be mounted, as shown on the external arch bow, or a pair of pulsating motors 20c and 20d may be mounted on the internal arch bow 14. The pulsating motors 20a, 20b, 20c and 20d may each include a housing "A" and a reciprocating shaft "B". The motors are interposed in the bows 10 and 14 with one end of the housing being secured to the corresponding bow, and the shaft B also being secured to the corresponding bow, so that the motor and its shaft is interposed between two separate ends of the corresponding bow. Then, when each motor is energized, the shaft B is caused to move reciprocally in and out with respect to the housing A, so as to set up the desired pulsating action.

As described above, when the posterior cervical extra oral appliance of FIG. 1 is used, a pulsating force is applied to the molars 21 and 22 to move the molars in a distal direction, as indicated by the arrows.

FIG. 2 is a representation of an anterior cervical extra oral appliance which, likewise, incorporates the concept of the present invention. The appliance of FIG. 2 includes a rigid retaining band 30 and a mouth brace including a pair of intraoral hooks 32 and 34. The hooks are coupled to the band 30 through spring units, such as the spring unit 36, so that a desired force may be inserted by the hooks on an arch wire 38, the arch wire being secured to selected molars by usual tooth bands 40 and 42. A pair of battery-operated electric pulsing units 44 and 46 are coupled to the intraoral hooks 32 and 34.

As shown, the appliance of FIG. 2 is attached to the anterior teeth, and the pulsation pressure delivered by way of the intraoral hooks 32 and 34 to the anterior maxillary or mandibular teeth serves to produce distal movement of the teeth.

The extra oral appliance of FIG. 3 is a face mask of the type manufactured and sold, for example, by Great Lakes Orthodontic Laboratories, Inc. of Buffalo, N.Y. The face mask includes a face crib 50 attached at one end to a pad 52 which engages the forehead of the wearer, and attached at its other end to a cup 54 which fits over the chin of the wearer. A mouth bow crib 56 is attached to the face crib 50. The purpose of the face mask of FIG. 3 is to move the maxillary and mandibular teeth in the forward direction. In accordance with the present invention, a battery-energized electric pulsating unit 58 is mounted on the mouth bow crib, as shown, so that a pulsating traction may be applied from the face mask to the maxillary or mandibular teeth in a mesial direction.

A removable palatal intraoral appliance is shown in FIG. 4 which includes an acrylic mouthpiece 60 which fits into the mouth over the palate. This appliance is commonly known as the Hawley type intraoral appliance. In the practice of the present invention, a battery-operated electrical pulsing unit 62 is mounted on, or embedded in the acrylic member. A pair of spring arms 64 and 66 extend from the pulsating unit between the teeth, as shown. A labial bow 68 is also mounted in place in the illustrated position.

Pressures are applied mesially or distally by the appliance of FIG. 4, using the palatal tissue as anchorage. When posterior teeth are to be moved mesially, the labial bow 68 embraces the anterior teeth using them as the anchorage for this type of movement. The spring arms 64 and 66 may vary so that they are capable of contacting the moving any teeth mesially, distally, buccally, or lingually.

The appliance of FIG. 4 is removable, and is worn only at the patient's convenience. As with the appliances described above, during the hours of non-wear, the battery energizing pulsing unit 62 may be recharged in a conventional recharging unit.

The mandibular intraoral appliance of FIG. 5 includes an acrylic mouthpiece 70, and an electric pulsating unit 72 mounted on, or embedded in, the mouthpiece. A labial bow 74 is mounted in place, as shown. A pair of spring arms 76 and 78 extend from the pulsating unit 72 between the teeth, as also shown; as in the embodiment of FIG. 4, pressures in all directions can be directed to the mandibular teeth by the appliance of FIG. 5.

The battery-operated electrical pulsating units referred to above may be of the type used, for example, in electric toothbrushes, such as fully described in U.S. Pat. Nos. 3,156,804; 3,142,852; and 3,187,360. As fully described in the patents, battery-operated electrical pulsating units are well known to the art. Such units comprise a housing and a shaft extending out from the housing, the shaft moving reciprocally in and out when the unit is energized. In the embodiment of FIG. 1, for example, the pulsating motor 20 may be mounted on the external bow, and its pulsating shaft may be attached to the internal bow, so as to achieve the desired pulsating action. The pulsating motors 20a-20d, on the other hand, may be interposed in the extra oral and internal bows, so that their housings are attached at one end, and their shafts are attached at the other end, so as to achieve the desired pulsating action. The pulsating units in the embodiments of FIGS. 2, 3, 4 and 5 may be similarly mounted.

The embodiments of FIGS. 6–10 use hydraulic fluid pre-sure to achieve the pulsating force on the tooth to be moved. In FIGS. 6 and 7, a tubular bow 80 is coupled to a tooth band 82 which surrounds the tooth 84 to be moved. The tubular bow 80 extends to an occlusal pad 86 which is mounted on a second tooth 88 on the opposite side of the arch. Appropriate hydraulic fluid is contained within the tubular bow 80, and within the occlusal pad 86. Each time a tooth contacts the occlusal pad 86, the hydraulic fluid will be moved in a first direction through the tubular bow to exert a force on the tooth 82, and each time the contact is removed, the hydraulic fluid will flow in the opposite direction through the tubular bow to remove the force. Therefore, the force exerted on the tooth 82 is in the nature of a pulsation. The wearer will involuntarily cause a tooth contact each time he swallows, which results normally in a minimum of 2,000 pulsations per day. The force of the pulsations can be varied by varying the diameter of the tubular bow 80, or the size of the occlusal pad 86.

The appliance of FIGS. 6 and 7 can be used in the maxillae and/or in the mandible. It can be unilateral or bilateral. The occlusal pad tends to unlock cusp contact, and makes it easier to move teeth without interference.

Therefore, in the embodiment of FIGS. 6 and 7, vertical occlusion pressure is delivered to the occlusal pad 86. The hydraulic fluid is forced into the tubular bow 80 and directed as a horizontal pressure on tooth 84 on the opposite side of the arch. This pulsation pressure on tooth 84 is repeated each time there is an occlusal contact on the occlusal pad 86. Occlusal contact takes place in the mastication of food and, as noted above, each time the wearer swallows. The frequency of occlusal contact produces a horizontal pulsation pressure delivered to the tooth 84 so that it may be moved orthodontally.

In the embodiment of FIG. 8, an occlusal pad 90 is mounted directly on the tooth 94 to be moved. The pad 90 is connected to a resilient tube 92 whose mesial end is formed into a spiral, as shown, to constitute a cyclic dissipating center. As in the previous embodiment, appropriate hydraulic fluid is contained within the pad 90.

Each time there is occlusal contact on the occlusal pad 90, hydraulic fluid is forced into the resilient tube 92. This spiral portion of tube 92, or cyclic dissipating center, expands as the occlusal force is applied to pad 90. Then, when the occlusal contact is removed, the resilient spiral dissipating center contracts by elastic force pulsing the tooth 94 to the left in FIG. 8, and forcing the hydraulic fluid back into the occlusal pad 90. In this manner, a pulsation force is delivered to the tooth 94 which moved the tooth distally. The force is delivered to the tooth after each occlusal contact and causes the tooth to be moved horizontally in a physiological pulsation manner. The resilient tube 92 is connected to tooth 94 through a telescoping sleeve (not shown) which allows the tooth to move distally and still be able to receive the pressure pulses.

When the occlusal pad 90 is mounted on the tooth which is being moved, as in the case in the embodiments of FIGS. 8, 9 and 10, it will tend to maintain the tooth in a constant vertical position during movement, rather than resulting in any extrusion or open bite problems.

The spiral end of the resilient tube 92 of the appliance of FIG. 8 is mounted on the acrylic mouthpiece 96 of a removable maxillary palatal appliance in the embodiment of FIG. 9. In this way, the mouthpiece 96 serves as an abutment from which maxillary posterior teeth, such as tooth 94, can be moved distally in a pulsational manner. In the embodiment of FIG. 10, the spiral end of the resilient tube 92 is anchored on the acrylic mouthpiece 98 of a removable mandibular appliance.

Then, in the same manner as the maxillary appliance of FIG. 9 houses the cyclic dissipation center, the mandibular appliance of FIG. 10 anchors the same center in the mandibular arch. In the lower arch, from occlusal contact, horizontal pressures are generated to move the posterior teeth, such as tooth 94, distally. To complete the mechanotherapy, it follows that after the molars have been moved distally, the anterior teeth can subsequently be moved distally from the anchored molars.

The embodiments of FIGS. 6–10 serve to translate occlusal vertical pressures of tooth contact into horizontal pulsation forces. Because most orthodontic problems arise due to discrepancies between tooth mass and arch length, or protrusion of anterior teeth, the pulsation forces can be directed to cause distallization of posterior molars after extraction of the third molars, and thus solve orthodontic problems without the need for bicuspid extraction. Because the pulsation pressure is physiological in nature, rather than pathological, the tooth movement will be faster, painless, require less orthodontic chair time, and result in no root resorption or horizontal bone loss.

It will be appreciated that while particular embodiments of the implementing the process invention have been shown and described, modifications may be made. It is intended in the claims to cover the modifications which come within the spirit and scope of the invention.

What is claimed is:

1. A method for producing orthodontic tooth movement which comprises introducing pressure impulses to the tooth of sufficient amplitude alternately to increase the tissue pressure in the periodontal membrane and adjacent bone tissue and to reduce the tissue pressure in the periodontal membrane and adjacent bone tissue so as to produce a pump-like action in the area surrounding the tooth cyclically to suck blood and tissue fluid into the area and to expel blood and tissue from the area so as to increase cellular action around the tooth.

* * * * *